United States Patent
Mossakowska et al.

(10) Patent No.: US 6,797,806 B2
(45) Date of Patent: *Sep. 28, 2004

(54) FRAGMENTS OF CR1 AND THEIR USE

(75) Inventors: Danuta Ewa Irena Mossakowska, Harlow (GB); Colin Michael Edge, Harlow (GB); Richard Anthony Godwin Smith, Herts (GB)

(73) Assignee: AdProTech Limited, Essex (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/142,043

(22) PCT Filed: Feb. 26, 1997

(86) PCT No.: PCT/EP97/00994

§ 371 (c)(1),
(2), (4) Date: Dec. 1, 1998

(87) PCT Pub. No.: WO97/31944

PCT Pub. Date: Sep. 4, 1997

(65) Prior Publication Data

US 2002/0142372 A1 Oct. 3, 2002

(30) Foreign Application Priority Data

Mar. 2, 1996 (GB) .......................... 96045182

(51) Int. Cl.$^7$ .................. C07K 14/47; A61K 38/16
(52) U.S. Cl. .................. 530/300; 530/380; 530/395; 530/402; 530/387.3; 424/185.1; 424/195.11
(58) Field of Search ................ 530/300, 380, 530/395, 402, 387.3; 424/185.1, 195.11

(56) References Cited

U.S. PATENT DOCUMENTS 5,116,964 A * 5/1992 Capon et al. ............... 536/27

* cited by examiner

Primary Examiner—Gary Kunz
Assistant Examiner—Fozia Hamud
(74) Attorney, Agent, or Firm—Heller Ehrman White & McAuliffe

(57) ABSTRACT

A polypeptide comprising a portion of the sequence of the general formula (I): CNPGSGGRKVFELVGEPSIYCTSNDDQVGIWSG, of 6–23 amino acids in length and comprising sequence a) and/or b): a) GGRKVF, b) FELVGEPSIY multimeric and chimeric derivatives, pharmaceutiocal compositions containing them and their use in therapy.

18 Claims, No Drawings

SEQUENCE LISTING

<160> NUMBER OF SEQ ID NOS: 8

<210> SEQ ID NO 1
<211> LENGTH: 33
<212> TYPE: PRT
<213> ORGANISM: Homo sapiens

<400> SEQUENCE: 1

Cys Asn Pro Gly Ser Gly Gly Arg Lys Val Phe Glu Leu Val Gly Glu
 1               5                  10                  15

Pro Ser Ile Tyr Cys Thr Ser Asn Asp Asp Gln Val Gly Ile Trp Ser
            20                  25                  30

Gly

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: peptide

<400> SEQUENCE: 2

Lys Lys Lys Lys Lys Lys Lys Ala
 1               5

<210> SEQ ID NO 3
<211> LENGTH: 75
<212> TYPE: PRT
<213> ORGANISM: Homo sapiens

<400> SEQUENCE: 3

Arg Ile Pro Cys Gly Leu Pro Pro Thr Ile Thr Asn Gly Asp Phe Ile
 1               5                  10                  15

Ser Thr Asn Arg Glu Asn Phe His Tyr Gly Ser Val Val Thr Tyr Arg
            20                  25                  30

Cys Asn Pro Gly Ser Gly Gly Arg Lys Val Phe Glu Leu Val Gly Glu
        35                  40                  45

Pro Ser Ile Tyr Cys Thr Ser Asn Asp Asp Gln Val Gly Ile Trp Ser
    50                  55                  60

Gly Pro Ala Pro Gln Cys Ile Ile Pro Asn Lys
65                  70                  75

<210> SEQ ID NO 4
<211> LENGTH: 21
<212> TYPE: PRT
<213> ORGANISM: Homo sapiens

<400> SEQUENCE: 4

Cys Asn Pro Gly Ser Gly Gly Arg Lys Val Phe Glu Leu Val Gly Glu
 1               5                  10                  15

Pro Ser Ile Tyr Cys
            20

```
<210> SEQ ID NO 5
<211> LENGTH: 17
<212> TYPE: PRT
<213> ORGANISM: Homo sapiens

<400> SEQUENCE: 5

Ser Gly Gly Arg Lys Val Phe Glu Leu Val Gly Glu Pro Ser Ile Tyr
 1               5                  10                  15

Cys

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: peptide

<400> SEQUENCE: 6

Lys Lys Lys Lys Lys Lys Ala
 1               5

<210> SEQ ID NO 7
<211> LENGTH: 8
<212> TYPE: PRT
<213> ORGANISM: Homo sapiens

<400> SEQUENCE: 7

Cys Gly Gly Arg Lys Val Phe Cys
 1               5

<210> SEQ ID NO 8
<211> LENGTH: 23
<212> TYPE: PRT
<213> ORGANISM: Homo sapiens

<400> SEQUENCE: 8

Phe Glu Leu Val Gly Glu Pro Ser Ile Tyr Ser Thr Ser Asn Asp Asp
 1               5                  10                  15

Gln Val Gly Ile Trp Ser Gly
                20
```

FRAGMENTS OF CR1 AND THEIR USE

This application is a § 371 PCT/EP97/00994, filed Feb. 26, 1997, (now WO 97/31944, published on Sep. 4, 1997); which is hereby incorporated by reference, in its entirety.

The present invention relates to polypeptides and their use in the diagnosis and therapy of disorders involving complement activity and various inflammatory and immune disorders.

Constituting about 10% of the globulins in normal serum, the complement system is composed of many different proteins that are important in the immune system's response to foreign antigens. The complement system becomes activated when its primary components are cleaved and the products alone or with other proteins, activate additional complement proteins resulting in a proteolytic cascade. Activation of the complement system leads to a variety of responses including increased vascular permeability, chemotaxis of phagocytic cells, activation of inflammatory cells, opsonization of foreign particles, direct killing of cells and tissue damage. Activation of the complement system may be triggered by antigen-antibody complexes (the classical pathway) or, for example, by lipopolysaccharides present in cell walls of pathogenic bacteria (the alternative pathway).

Complement activation (CA) is known to occur in a wide variety of acute inflammatory processes particularly those associated with ischaemia and reperfusion injury (Rossen et al., 1985 Circ. Res., 57, 119,; Morgan B. P., 1990 The biological effects of complement activation. In 'Complement, Clinical Aspects and Relevance to Disease', Academic Press, London.).

It is generally accepted that at least some of the components of the classical complement cascade can be detected by immunohistochemical methods in close association with senile plaques in AD brain (Eikelenboom et al., 1994, Neuroscience, 59, 561–568). There is good evidence for the involvement of C1, C3 and C4, but evidence for the presence of the C5–C9 membrane-attack complex (MAC) is not yet evident (Veerhuis et al, 1995, Vichows Arch. 426, 603–610). Cells of the CNS have been shown to synthesise complement components (for review see Barnum, 1995 Crit. Rev. Oral. Biol. Med 6, 132–146), and production of C3 is enhanced in response to incubation with bA4 peptide (Haga et al., 1993 Brain Res., 601, 88–94). Thus complement can be induced locally in the brain itself and is not necessarily derived solely from the plasma compartment.

Of particular interest is the fact that the bA4 peptide has been found to bind directly to the initial component of the complement cascade (C1q) and to initiate the whole of the classical complement system in vitro (including MAC) by an antibody-independent mechanism (Rogers et al., 1992, Proc. Nat. Acad. Sci. USA., 89, 10016–10020; Jianh et al., 1994, J. Immunol., 152, 5050–5059). This interaction appears to involve region 6–16 of βA4 and 14–26 of the collagen-like tail region of the C1q A chain. The lamer site is separate from the IgG-immune complex binding site located on the globular head domain of C1q. There is some evidence that fibrillar bA4 binds with higher affinity to C1q than monomeric peptide, potentially providing a rational basis for activation of complement in the disease process (Jiang et al., 1994, J. Immunol., 152, 5050–5059; Snyder et al., 1994, Exp. Neurol., 128, 136–142).

Complement receptor type 1 (CR1) has been shown to be present on the membranes of erythrocytes, monocytes/macrophages, granulocytes, B cells, some T cells, splenic follicular dendritic cells, and glomerular podocytes. CR1 binds to the complement components C3b and C4b and has also been referred to as the C3b/C4b receptor. The structural organisation and primary sequence of one allotype of CR1 is known (Klickstein et al., 1987, J. Exp. Med. 165:1095–1112, Klickstein et al., 1988, J. Exp. Med. 168:1699–1717; Hourcade et al., 1988, J. Exp. Med. 168:1255–1270, WO 89/09220, WO 91/05047). It is composed of 30 short consensus repeats (SCRs) that each contain around 60–70 amino acids. In each SCR, around 29 of the average 65 amino acids are conserved. Each SCR has been proposed to form a three dimensional triple loop structure through disulphide linkages with the third and first and the fourth and second half-cystines in disulphide bonds. CR1 is further arranged as 4 long homologous repeats (LHRs) of 7 SCRs each. Following a leader sequence, the CR1 molecule consists of the N-terminal LHR-A, the next two repeats, LHR-B and LHR-C, and the most C-terminal LHR-D followed by 2 additional SCRs, a 25 residue putative transmembrane region and a 43 residue cytoplasmic tail.

Based on the mature CR1 molecule having a predicted N-terminal glutamine residue, hereinafter designated as residue 1, the first four SCR domains of LHR-A are defined herein as consisting of residues 2–58, 63–120, 125–191 and 197–252, respectively, of mature CR1.

Hourcade et al., 1988, J. Exp. Med. 168:1255–1270 observed an alternative polyadenylation site in the human CR1 transcriptional unit that was predicted to produce a secreted form of CR1. The mRNA encoded by this truncated sequence comprises the first 8.5 SCRs of CR1, and encodes a protein of about 80 kDa which was proposed to include the C4b binding domain. When a cDNA corresponding to this truncated sequence was transfected into COS cells and expressed, it demonstrated the expected C4b binding activity but did not bind to C3b (Krych et al., 1989, FASEB J. 3:A368; Krych et al. Proc. Nat. Acad. Sci. 1991, 88, 4353–7). Krych et al., also observed a mRNA similar to the predicted one in several human cell lines and postulated that such a truncated soluble form of CR1 with C4b binding activity may be synthesised in humans.

In addition, Makrides et al. (1992, J. Biol. Chem. 267 (34) 24754–61) have expressed SCR 1+2 and 1+2+3+4 of LHR-A as membrane-attached proteins in CHO cells.

Several soluble fragments of CR1 have also been generated via recombinant DNA procedures by eliminating the transmembrane region from the DNAs being expressed (WO 89/09220, WO 91/05047). The soluble CR1 fragments were functionally active, bound C3b and/or C4b and demonstrated Factor I cofactor activity depending upon the regions they contained. Such constructs inhibited in vitro complement-related functions such as neutrophil oxidative burst, complement mediated hemolysis, and C3a and C5a production. A particular soluble construct, sCR1/pBSCR1c, also demonstrated in vivo activity in a reversed passive Arthus reaction (WO 89/09220, WO 91/05047; Yeh et al., 1991, J. Immunol. 146:250), suppressed post-ischemic myocardial inflammation and necrosis (WO 89/09220, WO 91/05047; Weisman et al., Science, 1990, 249:146–1511; Dupe, R. et al. Thrombosis & Haemostasis (1991) 65(6) 695.) and extended survival rates following transplantation (Pruitt & Bollinger, 1991, J. Surg. Res 50:350; Pruit et al., 1991 Transplantation 52; 868). Furthermore, co-formulation of sCR1/pBSCR1c with p-anisoylated human plasminogen-streptokinase-activator complex (APSAC) resulted in similar anti-haemolytic activity as sCR1 alone, indicating that the combination of the complement inhibitor sCR1 with a thrombolytic agent was feasible (WO 91/05047).

In a model of antibody-mediated demyelinating experimental allergic encephalomyelitis (ADEAE), systemic inhibition of CA using sCR1 over 6 days, produced improvements in clinical score and blocked CNS inflammation, demyelination and deposition of complement components (Piddlesden et al., 1994, J. Immunol. 152, 5477). ADEAE can be regarded as a model of acute relapse in multiple sclerosis (MS) and these striking results suggested possible applications for sCR1 in MS therapy despite the high molecular weight (245 kilodaltons) of this agent.

In a rat model of traumatic brain injury, complement inhibitor sCR1 (BRL55730) was shown to reduce myeloperoxidase activity (an indicator of neutrophil accumulation) following traumatic injury (Kaczorowska et al, 1995, J. Cerebral Blood Flow and Metabolism, 15, 860–864). This is suggested as demonstrating that complement activation is involved in the local inflammatory response.

Soluble polypeptides corresponding to part of CR1 having functional complement inhibitory, including antihaemolytic, activity have been described in WO94/00571 comprising, in sequence, one to four short consensus repeats (SCR) selected from SCR 1, 2, 3 and 4 of long homologous repeat A (LHR-A) s the only structurally and functionally intact SCR domains of CR1 and including at least SCR3.

According to the present invention there is provided a polypeptide comprising a portion of the sequence of the general formula (I): (SEQ ID NO: 1)

CNPGSGGRKVFELVGEPSIYCTSNDDQVGIWSG       (1)

of 6 to 23 amino acids in length and comprising sequence a) (residues 6–11 of SEQ ID NO: 1) and/or b) (residues 11–20 of SEQ ID NO: 1):

a) GGRKVF
b) FELVGEPSIY

The peptides of the invention are derived from the region of SCR3 of human CR1 between amino acids C154 to G186.

It is to be understood that variations in the amino acid sequence of the polypeptide of the invention by way of addition, deletion or conservative substitution of residues, including allelic variations, in which the biological activity of the polypeptide is retained, are encompassed by the invention. Conservative substitution is understood to mean the retention of the charge, hydrophobicity/hydrophilicity and size characteristics of the amino acid side chain, for example arginine replaced by histidine or lysine.

The polypeptide may be modified to have cysteine residues at the C and N termini to provide a molecule capable of forming a cyclic molecule bridged by a disulphide bond. The peptide may also be altered at specific amino acids to remove chemically reactive amino acids such as cysteine, or replace such amino acids by conservative substitutions such as serine.

The polypeptide may have chemically reactive amino acids such as cysteine, lysine or glutamic acid at the N or C-terminal ends optionally further derivatised or derivatisable to provide a route for chemical linkage to other peptides or chemicals. Preferably, the terminal amino acid is cysteine and a derivative is S-(2-pyridyl) dithio.

Enhanced activity may be achieved by forming multimerised polypeptides. According to the present invention there is provided a multimeric polypeptide comprising two or more, for example two to eight, polypeptides of the invention, linked to a core structure which may be a core peptide or multifunctional molecule. The core peptide is preferably a lysine derivative such as the 'MAP' peptide (Posnett, D. N. & Tam, J. P, Methods in Enzymology, 1989, 178, 739–746) exemplified by $(lys)_4(lys)_2$ lys ala (SEQ ID NO: 2) in which the first lysine has two further lysines linked to both alpha and epsilon amino groups and the second two lysines each have two further lysines thus giving a branched (dendritic) polymer with eight unsubstituted amino groups. Other examples of core structures include Tris (aminoethyl) amine and 1,2,4,5 benzene tetracarboxylic acid. Each polypeptide is lined to the core structure. Preferably, a cysteine-terminated peptide is linked to thiol-reactive core structure.

In a further aspect, the invention provides chimaeric polypeptides in which a polypeptide of the invention is inserted in or substituted for sequences not essential to the overall architecture or folding pathway of a host protein.

In one alternative the host protein contains one or more SCR repeat, such as an SCR-containing protein of the complement control protein family, for example factor H, C4 binding protein, decay accelerating factor, membrane cofactor protein or complement receptor 2. Such insertions or additions may be used as a a means of adding and/or enhancing anti-complement activity of the host protein. Preferably such substitutions or insertions are made into loop regions (predicted from secondary structure prediction algorithms, homology modelling of tertiary structure or by sequence alignments which identify variable-length insertions in an otherwise conserved sequence background) of the SCR-type module.

In another alternative the host protein is a plasma protein and the insertion or substitution may be used to confer anti-complement activity on the host protein and to alter the stability or pharmacokinetic behaviour of the inserted polypeptide in vivo. Suitable examples of such substitutions or insertions include those into a surface loop of an immunoglobulin Fc domain, a non-complementarity-determining region (CDR) of an Fab domain, a turn region of a kringle or growth factor domain or a beta-turn in a 'finger' domain such as those found in fibronectin.

The term 'polypeptide of the invention' will be used hereafter to refer to polypeptides derived from the sequence of general formula (I) as well as multimerised polypeptides and chimeric polypeptides of the invention.

In a further aspect, the invention provides a process for preparing a polypeptide according to the invention which process comprises expressing DNA encoding said polypeptide in a recombinant host cell and recovering the product, and thereafter optionally chemically linking the polypeptide to a core structure.

In particular, the process may comprise the steps of:
i) preparing a replicable expression vector capable, in a host cell, of expressing a DNA polymer comprising a nucleotide sequence that encodes said polypeptide;
ii) transforming a host cell with said vector;
iii) culturing said transformed host cell under conditions permitting expression of said DNA polymer to produce said polypeptide; and
iv) recovering said polypeptide.

The DNA polymer comprising a nucleotide sequence that encodes the polypeptide also forms part of the invention.

The process of the invention may be performed by conventional recombinant techniques such as described in Sambrook et al., Molecular Cloning: A laboratory manual 2nd Edition. Cold Spring Harbor Laboratory Press (1989) and DNA Cloning vols I, II and III (D. M. Glover ed., IRL Press Ltd).

The invention also provides a process for preparing the DNA polymer by the condensation of appropriate mono-, di- or oligomeric nucleotide units.

The preparation may be carried out chemically, enzymatically, or by a combination of the two methods, in vitro or in vivo as appropriate. Thus, the DNA polymer may be prepared by the enzymatic ligation of appropriate DNA fragments, by conventional methods such as those described by D. M. Roberts et al., in Biochemistry 1985, 24, 5090–5098.

The DNA fragments may be obtained by digestion of DNA containing the required sequences of nucleotides with appropriate restriction enzymes, by chemical synthesis, by enzymatic polymerisation, or by a combination of these methods.

Digestion with restriction enzymes may be performed in an appropriate buffer at a temperature of 20°–70° C., generally in a volume of 50 µl or less with 0.1–10 µg DNA.

Enzymatic polymerisation of DNA may be carried out in vitro using a DNA polymerase such as DNA polymerase 1 (Klenow fragment) in an appropriate buffer containing the nucleoside triphosphates dATP, dCTP, dGTP and dTFP as required at a temperature of 10°–37° C., generally in a volume of 50 µl or less.

Enzymatic ligation of DNA fragments may be carried out using a DNA ligase such as T4 DNA ligase in an appropriate buffer at a temperature of 4° C. to 37° C., generally in a volume of 50 µl or less.

The chemical synthesis of the DNA polymer or fragments may be carried out by conventional phosphotriester, phosphite or phosphoramidite chemistry, using solid phase techniques such as those described in 'Chemical and Enzymatic Synthesis of Gene Fragments—A Laboratory Manual' (ed. H. G. Gassen and A. Lang), Verlag Chemie, Weinheim (1982), or in other scientific publications, for example M. J. Gait, H. W. D. Matthes M. Singh, B. S. Sproat and R. C. Titmas, Nucleic Acids Research, 1982, 10, 6243; B. S. Sproat and W. Bannwarth, Tetrahedron Letters, 1983, 24, 5771; M. D. Matteucci and M. H. Caruthers, Tetrahedron Letters, 1980, 21, 719; M. D. Matteucci and M. H. Caruthers, Journal of the American Chemical Society, 1981, 103, 3185; S. P. Adams et al., Journal of the American Chemical Society, 1983, 105, 661; N. D. Sinha, J. Biernat, J. McMannus and H. Koester, Nucleic Acids Research, 1984, 12, 4539; and H. W. D. Matthes et al., EMBO Journal, 1984, 3, 801. Preferably an automated DNA synthesiser (for example, Applied Biosystems 381A Synthesiser) is employed.

The DNA polymer is preferably prepared by ligating two or more DNA molecules which together comprise a DNA sequence encoding the polypeptide.

The DNA molecules may be obtained by the digestion with suitable restriction enzymes of vectors carrying the required coding sequences.

The precise structure of the DNA molecules and the way in which they are obtained depends upon the structure of the desired product. The design of a suitable strategy for the construction of the DNA molecule coding for the polypeptide is a routine matter for the skilled worker in the art.

In particular, consideration may be given to the codon usage of the particular host cell. The codons may be optimised for high level expression in E. coli using the principles set out in Devereux et al., (1984) Nucl. Acid Res., 12, 387.

The expression of the DNA polymer encoding the polypeptide in a recombinant host cell may be carried out by means of a replicable expression vector capable, in the host cell, of expressing the DNA polymer. The expression vector is novel and also forms part of the invention.

The replicable expression vector may be prepared in accordance with the invention, by cleaving a vector compatible with the host cell to provide a linear DNA segment having an intact replicon, and combining said linear segment with one or more DNA molecules which, together with said linear segment, encode the polypeptide, under ligating conditions.

The ligation of the linear segment and more than one DNA molecule may be carried out simultaneously or sequentially as desired.

Thus, the DNA polymer may be preformed or formed during the construction of the vector, as desired. The choice of vector will be determined in part by the host cell, which may be prokaryotic, such as E. coli, or eukaryotic, such as mouse C127, mouse myeloma, chinese hamster ovary, fungi e.g. filamentous fungi or unicellular 'yeast' or an insect cell such as Drosophila. The host cell may also be in a trangeric animal. Suitable vectors include plasmids, bacteriophages, cosmids and recombinant viruses derived from, for example, baculoviruses or vaccinia.

The DNA polymer may be assembled into vectors designed for isolation of stable transformed mammalian cell lines expressing the fragment e.g. bovine papillomavirus vectors in mouse C127 cells, or amplified vectors in chinese hamster ovary cells (DNA Cloning Vol. II D. M. Glover ed. IRL Press 1985; Kaufman, R. J. et al., Molecular and Cellular Biology 5, 1750–1759, 1985; Pavlakis G. N. and Hamer, D. H. Proceedings of the National Academy of Sciences (USA) 80, 397–401, 1983; Goeddel, D. V. et al., European Patent Application No. 0093619, 1983).

The preparation of the replicable expression vector may be carried out conventionally with appropriate enzymes for restriction, polymerisation and ligation of the DNA, by procedures described in, for example, Sambrook et al., cited above. Polymerisation and ligation may be performed as described above for the preparation of the DNA polymer. Digestion with restriction enzymes may be performed in an appropriate buffer at a temperature of 20°–70° C., generally in a volume of 50 µl or less with 0.1–10 µg DNA.

The recombinant host cell is prepared, in accordance with the invention, by transforming a host cell with a replicable expression vector of the invention under transforming conditions. Suitable transforming conditions are conventional and are described in, for example, Sambrook et al., cited above, or "DNA Cloning" Vol. II, D. M. Glover ed., IRL Press Ltd, 1985.

The choice of transforming conditions is determined by the host cell. Thus, a bacterial host such as E. coli, may be treated with a solution of $CaCl_2$ (Cohen et al., Proc. Nat. Acad. Sci., 1973, 69, 2110) or with a solution comprising a mixture of RbCl, $MnCl_2$, potassium acetate and glycerol, and then with 3-[N-morpholino]-propane-sulphonic acid, RbCl and glycerol or by electoporation as for example described by Bio-Rad Laboratories, Richmond, Calif., USA, manufacturers of an electroporator. Mammalian cells in culture may be transformed by calcium co-precipitation of the vector DNA onto the cells or by using cationic liposomes.

The invention also extends to a host cell transformed with a replicable expression vector of the invention.

Culturing the transformed host cell under conditions permitting expression of the DNA polymer is carried out conventionally, as described in, for example, Sambrook et al., and "DNA Cloning" cited above. Thus, preferably the cell is supplied with nutrient and cultured at a temperature below 45° C.

The protein product is recovered by conventional methods according to the host cell. Thus, where the host cell is bacterial such as E. coli and the protein is expressed intracellularly, it may be lysed physically, chemically or enzymatically and the protein product isolated from the resulting lysate. Where the host cell is mammalian, the product is usually isolated from the nutrient medium.

Where the host cell is bacterial, such as *E. coli*, the product obtained from the culture may require folding for optimum functional activity. This is most likely if the protein is expressed as inclusion bodies. There are a number of aspects of the isolation and folding process that are regarded as important. In particular, the polypeptide is preferably partially purified before folding, in order to minimise formation of aggregates with contaminating proteins and minimise misfolding of the polypeptide. Thus, the removal of contaminating *E. coli* proteins by specifically isolating the inclusion bodies and the subsequent additional purification prior to folding are important aspects of the procedure.

The folding process is carried out in such a way as to minimise aggregation of intermediate-folded states of the polypeptide. Thus, careful consideration needs to be given to, among others, the salt type and concentration, temperature, protein concentration, redox buffer concentrations and duration of folding. The exact condition for any given polypeptide generally cannot be predicted and must be determined by experiment.

There are numerous methods available for the folding of proteins from inclusion bodies and these are known to the skilled worker in this field. The methods generally involve breaking all the disulphide bonds in the inclusion body, for example with 50 mM 2-mercaptoethanol, in the presence of a high concentration of denaturant such as 8M urea or 6M guanidine hydrochloride. The next step is to remove these agents to allow folding of the proteins to occur. Formation of the disulphide bridges requires an oxidising environment and this may be provided in a number of ways, for example by air, or by incorporating a suitable redox system, for example a mixture of reduced and oxidised glutathione.

Preferably, the inclusion body is solubilised using 8M urea, in the presence of mercaptoethanol, and protein is folded, after initial removal of contaminating proteins, by addition of cold buffer. A preferred buffer is 20 mM ethanolamine containing 1 mM reduced glutathione and 0.5 mM oxidised glutathione. The folding is preferably carried out at a temperature in the range 1 to 5° C. over a period of 1 to 4 days.

If any precipitation or aggregation is observed, the aggregated protein can be removed in a number of ways, for example by centrifugation or by treatment with precipitants such as ammonium sulphate. Where either of these procedures are adopted, monomeric polypeptide is the major soluble product.

If the bacterial cell secretes the protein, folding is not usually necessary.

Alternatively the polypeptide may be synthesised by conventional solid phase peptide synthesis, for example using an automated peptide synthesiser and Fmoc (9-fluorenylmethoxycarbonyl) chemistry on para-alkoxybenzyl alcohol (Wang) resin with the C-terminal amino acid pre-attached.

Accordingly, in a further aspect the invention provides a process for preparing a polypeptide of the invention which comprises condensing appropriate peptide units, and thereafter optionally chemically linking the polypeptide to a core structure.

In the multimeric polypeptide of the invention the polypeptides are preferably linked to the core peptide or multifunctional molecule by way of chemical bridging groups include those described in EP0109653 and EP0152736. The bridging group is generally of the formula:

$$-A-R-B- \quad (II)$$

in which each of A and B, which may be the same or different, represents —CO—, —C(=$NH_2^+$)—, maleimido, —S— or a bond and R is a bond or a linking group containing one or more —($CH_2$)— or meta- or para-disubstituted phenyl units.

Where the polypeptide and core peptide or multifunctional molecule both include a cysteine the chemical bridging group will take the form —S—S—. The bridge is generated by conventional disulphide exchange chemistry, by activating a thiol on the polypeptide and reacting the activated thiol with a free thiol on the core structure. Alternatively, the free thiol may be on the polypeptide and the activated group on the core structure. Such activation procedures make use of disulphides which generate stable thiolate anions upon cleavage of the S—S linkage and include reagents such as 2,2' dithiopyridine and 5,5'-dithio (2-nitrobenzoic acid, DTNB) which form intermediate mixed disulphides capable of further reaction with thiols to give stable disulphide linkages.

R may include moieties which interact with water to maintain the water solubility of the linkage and suitable moieties include —CO—NH—, —CO—NMe—, —S—S—, —CH(OH)—, —$SO_2$—, —$CO_2$—, —($CH_2CH_2$—O)$_m$— and —C(COOH)— where m is an integer of 2 or more.

Examples of R include —($CH_2$)$_r$—, —($CH_2$)$_p$—S—S—($CH_2$)$_q$— and —($CH_2$)$_p$—CH(OH)—CH(OH)—($CH_2$)$_q$—, in which r is an integer of at least 2, preferably at least 4 and p and q are independently integers of at least 2.

The bridging group of formula (II) may be derived from a linking agent of formula (III):

$$X-R_1-Y \quad (III)$$

in which $R_1$ is a linking group containing one or more —($CH_2$)— units and X and Y are functional groups reactable with surface amino acid groups, preferably a lysine or cysteine group, or the N-terminal amino group, or a protein attachment group.

Preferred agents are those where X and Y are different, known as heterobifunctional agents. Each end of the agent molecule is reacted in turn with each molecule to be linked in separate reactions. Examples of heterobifunctional agents of formula (III) include:

3-(2-pyridyldithio) propionic acid N-oxysuccinimide ester 4-(N-maleimido) caproic acid N-oxysuccinimide ester 3-(2-pyridyl) methyl propionimidate hydrochloride In each case Y is capable of reacting with a thiol group on a polypeptide, which may be a native thiol or one introduced as a protein attachment group.

The protein attachment group is a functionality derived by modification of a polypeptide with a reagent specific for one or more amino acid side chains, and which contains a group capable of reacting with a cleavable section on the other molecule. An example of a protein attachment group is a thiol group. An example of a cleavable section is a disulphide bond. Alternatively the cleavable section may comprise an α, βdihydroxy function.

As an example, the introduction of a free thiol function by reaction of a polypeptide or core structure with 2-iminothiolane, 3-(2-pyridyldithio) propionic acid N-oxysuccinimide ester (with subsequent reduction) or N-acetyl homocysteine thiolactone will permit coupling of the protein attachment group with a thiol-reactive B structure. Alternatively, the protein attachment group can contain a thiol-reactive entity such as the 6-maleimidohexyl group or a 2-pyridyl-dithio group which can react with a free thiol in X. Preferably, the protein attachment group is derived from protein modifying agents such as 2-iminothiolane that react with lysine ε-amino groups in proteins.

When X represents a group capable of reacting directly with the amino acid side chain of a protein, it is preferably an N-oxysuccinimidyl group. When X represents a group capable of reacting with a protein attachment group, it is preferably a pyridylthio group.

In the above processes, modification of a polypeptide to introduce a protein attachment group is preferably carried out in aqueous buffered media at a pH between 3.0 and 9.0 depending on the reagent used. For a preferred reagent, 2-iminothiolane, the pH is preferably 6.5–8.5. The concentration of polypeptide is preferably high (>10 mg/ml) and the modifying reagent is used in a moderate (1.1- to 5-fold) molar excess, depending on the reactivity of the reagent. The temperature and duration of reaction are preferably in the range 0°–40° C. and 10 minutes to 7 days. The extent of modification of the polypeptide may be determined by assaying for attachment groups introduced.

Such assays may be standard protein chemical techniques such as titration with 5,5'-dithiobis-(2-nitrobenzoic acid). Preferably, 0.5–3.0 moles of protein attachment group will be introduced on average per mole of polypeptide. The modified polypeptide may be separated from excess modifying agents by standard techniques such as dialysis, ultrafiltration, gel filtration and solvent or salt precipitation. The intermediate material may be stored in frozen solution or lyophilised.

Where a protein attachment group is introduced in this way, the bridging group (II) will be formed from a reaction of the linking agent (III) and the protein attachment group.

The polypeptide and core structure to be linked are reacted separately with the ling agent or the reagent for introducing a protein attachment group by typically adding an excess of the reagent to the polypeptide, usually in a neutral or moderately alkaline buffer, and after reaction removing low molecular weight materials by gel filtration or dialysis. The precise conditions of pH, temperature, buffer and reaction time will depend on the nature of the reagent used and the polypeptide to be modified. The polypeptide linkage reaction is preferably carried out by mixing the modified polypeptide and core structure in neutral buffer at a molar excess of polypeptide appropriate to the number of reactive functionalities in the core structure. Other reaction conditions e.g. time and temperature, should be chosen to obtain the desired degree of linkage. If thiol exchange reactions are involved, the reaction should preferably be carried out under an atmosphere of nitrogen. Preferably, UV-active products are produced (eg from the release of pyridine 2-thione from 2-pyridyl dithio derivatives) so that coupling can be monitored.

After the linkage reaction, the multimeric polypeptide can be isolated by a number of chromatographic procedures such as gel filtration, ion-exchange chromatography, affinity chromatography or hydrophobic interaction chromatography. These procedures my be either low pressure or high performance variants.

The multimeric polypeptide may be characterised by a number of techniques including low pressure or high performance gel filtration, SDS polyacrylamide gel electrophoresis or isoelectric focussing and mass spectrometry.

The polypeptide of this invention is useful in the treatment or diagnosis of many complement-mediated or complement-related diseases and disorders including, but not limited to, those listed below.

Disease and Disorders Involving Complement
Neurological Disorders
multiple sclerosis
stroke
Guillain Barré Syndrome
traumatic brain injury
Parkinson's disease
allergic encephalitis
Alzheimer's disease
Disorders of Inappropriate or Undesirable Complement Activation
haemodialysis complications
hyperacute allograft rejection
xenograft rejection
corneal graft rejection
interleukin-2 induced toxicity during IL-2 therapy
paroxysmal nocturnal haemoglobinuria
Inflammatory Disorders
inflammation of autoimmune diseases
Crohn's Disease
adult respiratory distress syndrome
thermal injury including burns or frostbite
uveitis
psoriasis
asthma
acute pancreatitis
vascular inflammatory diseases such as Kawasaki's disease
Post-Ischemic Reperfusion Conditions
myocardial infarction
balloon angioplasty
atherosclerosis (cholesterol-induced) & restenosis
hypertension
post-pump syndrome in cardiopulmonary bypass or renal haemodialysis
renal ischemia
intestinal ischaemia
Immune Complex Disorders and Autoimmune Diseases
rheumatoid arthritis
systemic lupus erythematosus (SLE)
SLE nephritis
proliferative nephritis
glomerulonephritis
haemolytic anemia
myasthenia gravis
Infectious Diseases or Sepsis
multiple organ failure
septic shock
Reproductive Disorders
antibody- or complement-mediated infertility
Wound Healing and Prevention of Scar Formation The present invention is also directed to a pharmaceutical composition comprising a therapeutically effective amount of a polypeptide of the invention, as above defined, and a pharmaceutically acceptable carrier or excipient.

The invention also provides a polypeptide of the invention for use as an active therapeutic substance and for use in the treatment of a disease or disorder associated with inflammation or inappropriate complement activation.

The present invention also provides a method of treating a disease or disorder associated with inflammation or inappropriate complement activation comprising administering to a subject in need of such treatment a therapeutically effective amount of a polypeptide of the invention.

In the above methods, the subject is a human or non-human mammal, preferably a human.

An effective amount of the polypeptide for the treatment of a disease or disorder is in the dose range of 0.01–100 mg/kg; preferably 0.1 mg–10 mg/kg.

For administration, the polypeptide should be formulated into an appropriate pharmaceutical or therapeutic composition. Such a composition typically contains a therapeutically active amount of the polypeptide and a pharmaceutically acceptable excipient or carrier such as saline, buffered saline, dextrose, or water. Compositions may also comprise specific stabilising agents such as sugars, including mannose and mannitol, and local anaesthetics for injectable compositions, including, for example, lidocaine.

Further provided is the use of a polypeptide of the invention in the manufacture of a medicament for the treatment of a disease or disorder associated with inflammation or inappropriate complement activation.

The present invention also provides a method for treating a thrumbotic condition, in particular acute myocardial infarction, in a subject in need of such treatment. This method comprises administering to a subject in need of this treatment an effective amount of a polypeptide of the invention and an effective amount of a thrombolytic agent. Such methods and uses may be carried out as described in WO 91/05047.

This invention further provides a method for treating adult respiratory distress syndrome (ARDS) in a subject in need of such treatment, comprising administering to the patient an effective amount of a polypeptide of the invention.

The invention also provides a method of delaying hyperacute allograft or hyperacute xenograft rejection in a subject in need of such treatment which receives a transplant by administering an effective amount of a polypeptide of the invention. Such administration may be to the patient or by application to the transplant prior to implantation.

The invention yet further provides a method of treating wounds in a subject in need of such treatment by administering by either topical or parenteral e.g. intravenous routes, an effective amount of a polypeptide of the invention.

The invention still further provides a method of treating Alzheimer's Disease by administering to a subject in need of such treatment an effective amount of a polypeptide of the invention.

This invention also provides a method of treating CNS inflammatory disorders such as those associated with ischaemic stroke by administering to a subject in need of such treatment an effective amount of a polypeptide of the invention.

METHODS

SDS Polyacrylamide Gel Electrophoresis

Novex precast gels 4–20% were purchased from British Biotechnology and used in Xcell II electrophoresis cells according to the manufacturers instructions.

Peptide Synthesis

Peptides were synthesised by the solid phase technique using an Applied Biosystems 430A peptide synthesiser and Fmoc (9-fluorenylmethoxycarbonyl) chemistry on para-alkoxybenzyl alcohol (Wang) resin with the C-terminal amino acid pre-attached. The resin was treated with benzoic anhydride (2 mmol) in the presence of N,N-dicyclohexylcarbodiimide (1 mmol) and 4-dimethylaminopyridine (0.04 mmol) in N-methylpyrrolidone (NMP) and N,N-dimethylformamide (DMF) in order to block any residual free hydroxy groups prior to chain elongation. Each single-coupling cycle consisted of the following steps: 1. The resin was washed with NMP (x1); 2. Fmoc deprotection was carried out with two consecutive treatments (3 min and 15 min) of the resin using a solution of piperidine in NMP (starting concentration 20% v/v); 3. The resin was washed with NMP (x5); 4. The resin was coupled (60 min) with a solution of the preactivated amino acid (1 mmol) in NMP and DMF; 5. The resin was washed with NMP (x7). In the case of a double-coupling cycle, steps 4 and 5 were conducted twice. Fmoc amino acids (1 mmol) were pre-activated with 2-(1H-benzotriazol-1-yl)-1,1,3,3-tetramethyl uronium hexafluorophosphate (HBTU) (1 mmol) in the presence of 1-hydroxybenzotriazole (HOBt) (1 mmol) and N,N-diisopropylethylamine (DIEA) (2 mmol) for 6 to 12 min. After chain elongation, the Fmoc group was removed. The side chain protection used was 2,2,5,7,8-pentamethylchroman-6-sulphonyl (Pmc) for arginine, trityl for asparagine, glutamine and cysteine, tert-butyloxycarbonyl for lysine and tryptophan, and tert-butyl for serine, threonine, aspartic acid and glutamic acid. All residues were double-coupled unless stated.

Cleavage from the Resin

The ice-cooled peptidyl resin was treated with ice-cooled cleavage mixture A or B (10 ml) and stirred for 2 h at room temperature. The mixture was filtered and the filtrate evaporated in vacua to a low volume (3 to 5 ml) of solution. This was azeotroped in vacuo with dry toluene (x 2) and the residual oil triturated with dry diethyl ether (3×50 ml) to give a white precipitate. This was collected and dried in vacua to remove any trace of diethyl ether prior to lyophilisation from dilute aqueous acetic acid. The cleavage mixtures used were A: TFA/water/thioanisole/1,2-ethanedithiol (EDT)/phenol (88.9:4.4:4.4:2.2:6.7 v/v/v/v/w); B: ITA/water/EDT (75:5:20 v/v/v).

High Performance Liquid Chromatography (HPLC)

Separations were carried out using a Gilson gradient system with detection at 220 nm. Analytical HPLC was conducted on a Spherisorb C-18 column (25 cm×4.6 mm id) eluted at 1 ml/min and preparative HPLC was conducted on a Spherisorb C-8 column (25 cm×10 mm id) eluted at 4 ml/min unless stated, with eluents A=0.1% aqueous TFA and B=acetonitrile. Gradients used were A: isocratic elution for min at 10% B followed by a 45 min linear gradient to 60% B; B: isocratic elution for 5 min at 10% B followed by a 45 min linear gradient to 80% B; C: isocratic elution for 5 min at 10% B followed by a 50 min linear gradient to 50% B; D: isocratic elution for 1 min at 10% B followed by a 30 min linear gradient to 80% B; E: isocratic elution for 5 min at 15% B followed by a 60 min linear gradient to 30% B; F: isocratic elution for 1 min at 30% B followed by a 30 min linear gradient to 40% B; G: isocratic elution for 5 min at 10% B followed by a 60 min linear gradient to 40% B; H: isocratic elution for 5 min at 1% B followed by a 60 min linear gradient to 35% B; I: isocratic elution for 5 min at 5% B followed by a 60 min linear gradient to 30% B; J: isocratic elution for 1 min at 20% B followed by a 30 min linear gradient to 30% B.

EXAMPLES

Numbering of peptide residues corresponds to that of human CD35, (C3b/C4b receptor, CR1) (Klickstein et al., 1987, J. Exp. Med. 165:1095–1112; Klickstein et al., 1988, J. Exp. Med 168:1699–1717; Hourcade et al., 1988, J. Exp. Med. 168: 1255–1270). By this numbering, SCR3 of LHR-A is R122-K196:(SEQ ID NO: 3)

```
Arg Ile Pro Cys Gly Leu Pro Pro Thr Ile Thr Asn Gly Asp Phe
122             130

Ile ser Thr Asn Arg Glu Asn Phe His Tyr Gly Ser Val Val Thr Tyr
            140                             150

Arg Cys Asn Pro Gly Ser Gly Gly Arg Lys Val Phe Glu Leu Val Gly
                        160

Glu Pro Ser Ile Tyr Cys Thr Ser Asn Asp Asp Gln Val Gly Ile Trp
    170                             180

Ser Gly Pro Ala Pro Gln Cys Ile Ile Pro Asn Lys
                190                     196
```

Peptide sequences are presented conventionally with N terminal residues to the left.

Example 1

C154–C174 (E1a Linear Peptid, E1b Cyclic Peptide

CNPGSGGRKVFELVGEPSIYC    (E1)(SEQ ID NO: 4)

E1 contains sequence which spans residues C154-C174 of mature human CR1 which correspond to the second and third cysteines of SCR3. These two cysteines do not normally form a disulphide in wild type CR1 as the C154 pairs with C191 and C174 with the C125.

1a Synthesis of E1

Stepwise assembly from Fmoc-Cys(Trt)-resin (0.20 g; 0.10 mmol) gave the 21-residue peptidyl resin with the N-terminal Fmoc group removed (0.57 g). The peptidyl resin (0.28 g) was cleaved using mixture A to give crude solid (0.14 g) after lyophilisation. The crude product was purified by gel filtration over Sephadex G25 (column 83 cm×2.5 cm id; detection at 220 nm) using 1M aqueous acetic acid as eluent. The peptide eluted as a single peak which was split into six fractions (combined weight 0.082 g; 49%): A (11 mg), B (22 mg), C (17 mg), D (24 mg), E (4 mg) and F (4 mg).

1b Characterization of E1

HPLC analysis using gradient F showed the presence of three peaks of retention times 17.8 min (peak 1), 18.6 min (peak 2) and 19.8 min (peak 3) in each fraction in proportions as shown:

| Fraction | Peak 1 | Peak 2 | Peak 3 | Earlier-eluting material |
|---|---|---|---|---|
| A | 6 | 15 | 61 | 18 |
| B | 15 | 11 | 61 | 13 |
| C | 36 | 14 | 50 | — |
| D | 49 | 16 | 35 | — |
| E | 72 | 20 | 8 | — |
| F | 54 | 14 | 6 | 26 |

Peaks 1 and 3 were shown to be a reduced and oxidised form of the peptide respectively by treatment with dithiothreitol (DT) and with dimethylsulphoxide (DMSO). Peak 2 was an unknown contaminant which was not affected by DTT nor DMSO. An aqueous solution of fraction B (pH 7.5) was treated with excess DTT; HPLC after 6 h using gradient F showed peak 1 increased whilst peak 3 decreased. Fraction B was treated with an aqueous solution of DMSO (20% v/v); HPLC using gradient F after 11 h showed the disappearance of peak 1 whilst peak 3 increased. An aqueous solution of fraction E (pH 7.5) was treated with excess DTT; HPLC after 5.8 h using gradient F showed the disappearance of peak 3 whilst peak 1 increased. Fraction E was treated with an aqueous solution of DMSO (20% v/v); HPLC using gradient F after 12 h showed the disappearance of peak 1 whilst peak 3 increased.

Electrospray mass spectrometry gave evidence that peaks 1 and 3 were the linear (E1a) and cyclic (E1b) forms of the peptide respectively.

Fraction A gave ions corresponding to $[M+2H]^{2+}$ at m/z 1105.8 (rel. intensity 53%, deconvoluted corresponds to mw 2209.6, calculated for cyclic form 2209.0), m/z 1106.3 (66%, 2210.6), and m/z 1106.8 (53%, 2211.6, calculated for linear form 2210.0).

Fraction C gave ions corresponding to $[M+2H]^{2+}$ at m/z 1105.8 (41%, 2209.6), m/z 1106.4 (66%, 2210.8), m/z 1106.9 (100%, 2211.8), m/z 1107.3 (98%, 2212.6), and m/z 1107.8 (75%, 2213.6).

Fraction F gave ions corresponding to $[M+2H]^{2+}$ at m/z 1106.8 (98%, 2210.6), m/z 1107.3 (99%, 2212.6) and m/z 1107.7 (83%, 2213.4).

Amino acid analysis: Fraction A: Asx 1.0 (theoretical 1), Glu 2.4 (2), Ser 2.3 (2), Gly 4.2 (4), Arg 1.3 (1), Pro 2.2 (2), Tyr 0.9 (1), Val 1.5 (2), Cys 1.1 (2), Ile 1.1 (1), Leu 1.3 (1), Phe 0.1 (1), Lys 1.7 (1). Fraction C: Asx 1.1, Glu 2.5, Ser 2.1, Gly 4.0, Arg 1.2, Pro 2.1, Tyr 1.0, Val 1.6, Cys 1.1, Ile 1.1, Leu 1.3, Phe 0.1, Lys 1.8. Fraction F: Asx 1.1, Glu 2.4, Ser 2.3, Gly 4.1, Arg 1.2, Pro 2.4, Tyr 1.1, Val 1.4, Cys 0.9, Ile 1.3, Leu 1.1, Phe 0.1, Lys 1.6. (Note: Cys partially destroyed and Val-Phe bond only partially hydrolysed on acid hydrolysis.)

Example 2

S158–C174 (E2, SEQ ID NO:5)

SGGRKVFELVGEPSIYC    (E2)

This peptide spans the sequence from mature human CR1 S158 to C174.

2a Synthesis of E2

Stepwise assembly from Fmoc-Cys(Trt)-resin (0.49 g; 0.25 mmol) gave the 17-residue peptidyl resin with the N-terminal Fmoc group removed (1.03 g). Residues $Ser^1$, $Gly^{2,11}$, $Phe^7$, $Glu^{8,12}$ and $Pro^{13}$ were single-coupled. The peptidyl resin (0.51 g) was cleaved using mixture A to give crude solid (0.22 g) after lyophilisation. Purification of 0.072 g by preparative HPLC using gradients A, B and C gave purified solid (0.048 g; 66%).

2b Characterisation of E2

The product was >95% pure by analytical HPLC and had a retention time of 18.6 min using gradient D. Its identity was verified by observation of a [M+H]$^+$ ion in the FAB mass spectrum at m/z 1842 and by an amino acid analysis of Glx 1.97 (theoretical 2), Ser 1.86 (2), Gly 2.85 (3), Arg 1.13 (1), Pro 1.08 (1), Tyr 0.94 (1), Val 1.82 (2), Ile 0.99 (1), Leu 1.12 (1), Phe 1.1 (1), Lys 1.14 (1). (Cys not calculated due to its destruction on acid hydolysis.)

Example 3

Multiple Antigen Peptide (MAP)-E2 conjugate (E3)

To potentiate the activity of S158–C174 (E2), multiple binding sites were created by crosslinking E2 to a lysine core residue.

3a Derivatisation of MAP Peptide.

(i) N-(2-Pyridyl)dithiopropionyl MAP

MAP peptide (structure (Lys)$_4$ (Lys)$_2$ Ala-OH) (SEQ ID NO: 6) was purchased from Peptide and Protein Research, Exeter, UK. Peptide (9.8 mg, 10 micromoles) was dissolved in a mixture of dry dimethysulphoxide (DMSO, 100 microliters) and dry ACS-grade pyridine (200 microliters) in which had been dissolved 3-(2-pyridyl)dithiopropionic acid N-oxysuccinimide ester (Pharmacia, 25 mg, 80 micromoles, 1 mol equivalent to free amino groups in the MAP peptide). The clear solution was agitated gently overnight (15 h) at ambient temperature (~22° C.) and then stored at –80° C.

(ii) Conjugation to E2

Peptide E2 (as above, 7.4 mg, 4 micromoles) was dissolved in a mixture of dry DMSO (180 microliters) and dry ACS-grade pyridine (90 microliters) and the above PDP-MAP (15 microliters of solution, ~0.5 micromoles, ~4 micromoles PDP-equivalent) added. The mixture was agitated under dry nitrogen for 6 h at ambient temperature and a slight yellow colour was noted. It was then diluted to a final volume of 1.5 ml with 20 mM Ammonium Bicarbonate pH 7.4 at 4° C. The slightly cloudy solution was applied to a 1×10 cm column of Sephadex G-25m equilibrated and eluted with the ammonium bicarbonate buffer at 4° C. Fractions eluting between 2.5 and 5.5 ml, 5.5 and 7.5 ml and 7.5 and 9.0 ml were collected and lyophilised. Only the first of these contained measurable solid as a white powder (approx 14 mg).

3b Characterisation of Map-E2 Conjugate

The elution position of the conjugate on the Sephadex G-25 column suggested an effective molecular weight of ~10,000. This corresponds to a minimum of 4 E2 units disulphide-linked to the MAP (theoretical M$_r$ 9910). The maximum substition is 8 units/MAP (theoretical M$_r$ 17,750).

Example 4

C-(G159–F164)-C (E4, SEQ ID NO:7)

CGGRKVFC　　　　　　　　　　　　　　　　(E4)

This sequence spans residues of G159–F164 of mature human CR1. To enable circularisation cysteine has been added to the N and C-terminal ends of the peptide.

4a Synthesis of E4

Stepwise assembly from Fmoc-Cys(Trt)resin (0.49 g; 0.25 mmol) gave the 8-residue peptidyl resin with the N-terminal Fmoc group removed (0.74 g). Residues Gly$^{2,3}$ were single-coupled. The peptidyl resin (0.68 g) was cleaved using mixture A to give crude solid (0.22 g) after lyophilisation. Purification by preparative HPLC using gradients G, H and I gave purified solid (0.017 g; 8.6%).

4b Characterisation of E4

The product was >90% pure by analytical HPLC and had a retention time of 14.6 min using gradient J. The product was shown to be in an oxidised form by treatment with DTT and with DMSO. An aqueous solution of the product (pH 7.5) was treated with excess DTT; HPLC after 2.3 h using gradient J showed the peak at RT 14.6 min decreased whilst a new peak at RT 15.0 min appeared. The product was treated with an aqueous solution of DMSO (20% v/v); HPLC using gradient J after 1.3 h showed no change. Its identity as the cyclic peptide was verified by observation of a [M+H]$^+$ ion in the FAB mass spectrum at m/z 868.

Example 5

F164–G186 (C174S) (E5, SEQ ID NO:8)

FELVGEPSIYSTSNDDQVGIWSG　　　　　　(5)

This peptide spans the residues F164–G186 of mature human CR1. C174 has been substituted with serine.

5a Synthesis of E5

Stepwise assembly from Fmoc-Gly-resin (0.14 g; 0.10 mmol) gave the 23-residue peptidyl resin with the N-terminal Fmoc group removed (0.51 g). Residues Phe$^1$, Glu$^2$, Gly$^5$, Pro$^7$, Tyr$^{10}$, Ser$^{13,22}$, Asn$^{14}$ and Asp$^{15,16}$ were single-coupled. The peptidyl resin (0.24 g) was cleaved using mixture B to give crude solid (0.14 g) after lyophilisation. Purification by preparative HPLC on a Spherisorb C-18 column (25 cm×4.6 mm id) using gradient E gave purified solid (0.0039 g; 3.3%).

5b Characterisation of E5

The product was >90% pure by analytical HPLC and had a retention time of 12.2 min using gradient F. Its identity was verified by observation of a [M+H]$^+$ ion in the FAB mass spectrum at m/z 2501 and by an amino acid analysis of Asx 2.91 (theoretical 3), Glx 3.01 (3), Ser 3.99 (4), Gly 2.88 (3), Thr 1.07 (1), Pro 1.05 (1), Tyr 0.87 (1), Val 2.47 (2), Ile 1.75 (2), Leu 0.97 (1), Phe 1.00 (1). (Trp not calculated due to its destruction on acid hydrolysis.)

Biological Activity

Anti-Complement Activity Measured By the Haemolysis of Sheep Erythrocytes

Functional activity of complement inhibitors was assessed by measuring the inhibition of complement mediated lysis of sheep erythrocytes sensitised with rabbit antibodies (obtained from Diamedix Corporation, Miami, USA). Human serum diluted 1/125 in 0.1 M Hepes pH 7.4/0.15 M NaCl buffer was the source of complement and was prepared from a pool of volunteers essentially as described in (Dacie & Lewis, 1975). Briefly, blood was warmed to 37° C. for 5 minutes, the clot removed and the remaining serum clarified by centrifugation. The serum fraction was split into small aliquots and stored at –196° C. Aliquots were thawed as required and diluted in the Hepes buffer immediately before use. Where indicated, nitrogen gas or helium gas were bubbled through the buffer for approximately 30 minutes after which the bottle containing the buffer was stoppered.

Inhibition of complement-mediated lysis of sensitised sheep erythrocytes was measured using a standard haemolytic assay using a v-bottom microtitre plate format as follows, essentially as described by Weisman et al (1990) Science 249 146–151.

50 ul of a range of concentrations of inhibitor diluted in Hepes buffer were incubated with 50 ul of the 1/125. 100 ul of prewarmed sensitised sheep erythrocyes were added and samples incubated for 1 hour at 37° C. in a final reaction volume of 200 ul. Samples were spun at 300 g at 4° C. for 15 minutes before transferring 150 ul of supernatant to flat bottom microtitre plates and determining the absorption at 410 nm, which reflects the amount of lysis in each test solution. Maximum lysis was determined by incubating serum with erythrocytes in the absence of any inhibitor (E+S) from which the proportion of background lysis had been subtracted (determined by incubating erythrocytes with buffer (E). The background lysis by inhibitor was assessed by incubating inhibitor with erythrocytes (E+I) and then subtracting that from test samples (E+I+S). Inhibition was expressed as a fraction of the total cell lysis such that IH50 represents the concentration of inhibitor required to give 50% inhibition of lysis.

Maximum Lysis: A max=(E+S)−(E)
Lysis in presence of inhibitor: Ao=(E+I+S)−(E+I)
Amount of inhibition: IH=Amax−Ao/Amax

What is claimed is:

1. A polypeptide having only a partial sequence from short consensus repeat 3 of complement receptor 1, wherein the polypeptide comprises a 6 to 23 amino acid portion of SEQ ID NO: 1, and wherein the polypeptide has at least one amino acid sequence selected from the group consisting of:
   (a) amino acids 6–11 OF SEQ ID NO: 1, and
   (b) amino acids 11–20 of SEQ ID NO: 1.

2. The polypeptide according to claim 1, further comprising a cysteine residue at the carboxyl terminus and the amino terminus of the polypeptide, thereby providing a capability to form a cyclic polypeptide via formation of a disulfide bond.

3. The polypeptide according to claim 1, further comprising an additional amino acid residue located at least one position selected from the group consisting of the carboxyl terminus and the amino terminus of the polypeptide, wherein the additional amino acid residue is selected from the group consisting of cysteine, lysine, glutamic acid, arginine, asparagine, glutamine, tryptophan, serine, threonine and aspartic acid.

4. The polypeptide according to claim 3, wherein the additional amino acid residue is derivatized or derivatizable.

5. The polypeptide according to claim 4, wherein the terminal amino acid residue is cysteine derivatized with S-(2-pyridyl) dithio.

6. A multimeric polypeptide having only a partial sequence from short consensus repeat 3 of complement receptor 1, wherein the polypeptide comprises at least two polypeptide constituents that comprise a 6 to 23 amino acid portion of SEQ ID NO: 1, and wherein the polypeptide constituents have at least one amino acid sequence selected from the group consisting of:
   (a) amino acids 6–11 OF SEQ ID NO: 1, and
   (b) amino acids 11–20 of SEQ ID NO: 1, wherein the polypeptide constituents do not comprise a mature short consensus repeat-3 and the polypeptide constituents are covalently linked to a core structure selected from the group consisting of a lysine derivative, tris (aminoethyl) amine and 1,2,4,5 benzene tetracarboxylic acid.

7. The multimeric polypeptide according to claim 6, wherein the core structure comprises a multiple antigen peptide (MAP).

8. The multimeric polypeptide according to claim 6, wherein the multimeric polypeptide comprises at least two and no more than eight polypeptide constituents.

9. The multimeric polypeptide according to claim 6, wherein the MAP peptide comprises $(Lys)_4 (Lys)_2 Ala\text{-}OH$.

10. A chimeric polypeptide comprising a host protein and as an insert a polypeptide having only a partial sequence from short consensus repeat 3 of complement receptor 1, wherein the polypeptide having only a partial sequence from short consensus repeat 3 of complement receptor 1 comprises a 6 to 23 amino acid portion of SEQ ID NO: 1, wherein the polypeptide having only a partial sequence from short consensus repeat 3 of complement receptor 1 has at least one amino acid sequence selected from the group consisting of:

(a) amino acids 6–11 of SEQ ID NO: 1, and (b) amino acids 11–20 of SEQ ID NO: 1, wherein the polypeptide having only a partial sequence from short consensus repeat 3 of complement receptor 1 is inserted into a non essential region of the host protein.

11. The chimeric polypeptide according to claim 10, wherein the host protein contains at least one short consensus repeat of complement receptor 1.

12. The chimeric polypeptide according to claim 10, wherein the host protein is a plasma protein.

13. The polypeptide according to claim 1, wherein the polypeptide is selected from the group consisting of:

linear CNPGSGGRKVFELVGEPSIYC (SEQ ID NO: 4);

cyclic CNPGSGGRKVFELVGEPSIYC (SEQ ID NO: 4);

SGGRKVFELVGEPSIYC (SEQ ID NO: 5);

CGGRKVFC (SEQ ID NO: 7); and

FELVGEPSIYSTSNDDQVGIWSG (SEQ ID NO: 8).

14. A process for preparing a polypeptide having only a partial sequence from short consensus repeat 3 of complement receptor 1, wherein the polypeptide comprises a 6 to 23 amino acid portion of SEQ ID NO: 1, and wherein the polypeptide has at least one amino acid sequence selected from the group consisting of:

(a) amino acids 6–11 of SEQ ID NO: 1, and (b) amino acids 11–20 of SEQ ID NO: 1, comprising the steps of:

condensing peptide units, in solid phase synthesis to form the polypeptide, and recovering the polypeptide.

15. A process for preparing a polypeptide having only a partial sequence from short consensus repeat 3 of complement receptor 1, wherein the polypeptide comprises a 6 to 23 amino acid portion of SEQ ID NO: 1, and wherein the polypeptide has at least one amino acid sequence selected from the group consisting of:

(a) amino acids 6–11 of SEQ ID NO: 1, and (b) amino acids 11–20 of SEQ ID NO: 1, comprising the step of: expressing DNA encoding the polypeptide in a recombinant host cell, and recovering the polypeptide.

16. An isolated polynucleotide encoding a polypeptide having only a partial sequence from short consensus repeat 3 of complement receptor 1, wherein the polypeptide comprises a 6 to 23 amino acid portion of SEQ ID NO: 1, and wherein the polypeptide has at least one amino acid sequence selected from the group consisting of:

(a) amino acids 6–11 of SEQ ID NO: 1, and (b) amino acids 11–20 of SEQ ID NO: 1.

17. The polynucleotide according to claim 16, wherein the polynucleotide is in an expression vector.

18. The polynucleotide according to claim 16, wherein the polynucleotide is in an expression vector and the expression vector is in a host cell, by transformation or transfection.

* * * * *